(12) United States Patent
Hua

(10) Patent No.: US 9,642,552 B2
(45) Date of Patent: *May 9, 2017

(54) INSERTION OF MEDICAL DEVICES THROUGH NON-ORTHOGONAL AND ORTHOGONAL TRAJECTORIES WITHIN THE CRANIUM AND METHODS OF USING

(71) Applicant: Sherwin Hua, Hillsborough, CA (US)

(72) Inventor: Sherwin Hua, Hillsborough, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/645,167

(22) Filed: Mar. 11, 2015

(65) Prior Publication Data
US 2015/0245781 A1 Sep. 3, 2015

Related U.S. Application Data

(63) Continuation of application No. 13/318,462, filed as application No. PCT/US2010/061531 on Dec. 21, 2010, now Pat. No. 9,179,875.
(Continued)

(51) Int. Cl.
*A61B 5/0478* (2006.01)
*A61B 17/16* (2006.01)
(Continued)

(52) U.S. Cl.
CPC .......... *A61B 5/0478* (2013.01); *A61B 5/0482* (2013.01); *A61B 5/4064* (2013.01);
(Continued)

(58) Field of Classification Search
CPC .. A61B 5/0478; A61B 17/1695; A61N 1/0531
(Continued)

(56) References Cited

U.S. PATENT DOCUMENTS 5,300,076 A 4/1994 Leriche
5,324,316 A 6/1994 Schulman et al.
(Continued)

FOREIGN PATENT DOCUMENTS

CN 101022848 8/2007
GB 2330078 4/1999
(Continued)

OTHER PUBLICATIONS

Sep. 22, 2014 Office Action for Japanese Application No. 2012-546147 Filed Jun. 20, 2012.
(Continued)

*Primary Examiner* — Carl H Layno
*Assistant Examiner* — Erin M Piateski
(74) *Attorney, Agent, or Firm* — Knobbe, Martens, Olson & Bear LLP

(57) ABSTRACT

The invention comprises an elongated device adapted for insertion, including self-insertion, through the body, especially the skull. The device has at least one effector or sensor and is configured to permit implantation of multiple functional components through a single entry site into the skull by directing the components at different angles. The device may be used to provide electrical, magnetic, and other stimulation therapy to a patient's brain. The lengths of the effectors, sensors, and other components may completely traverse skull thickness (at a diagonal angle) to barely protrude through to the brain's cortex. The components may directly contact the brain's cortex, but from there their signals can be directed to targets deeper within the brain. Effector lengths are directly proportional to their battery size and ability to store charge. Therefore, longer angled electrode effectors not limited by skull thickness permit longer-lasting batteries which expand treatment options.

5 Claims, 11 Drawing Sheets

Related U.S. Application Data

(60) Provisional application No. 61/288,619, filed on Dec. 21, 2009.

(51) Int. Cl.
*A61N 1/05* (2006.01)
*A61B 5/00* (2006.01)
*A61B 5/0482* (2006.01)
*A61N 1/36* (2006.01)

(52) U.S. Cl.
CPC .......... *A61B 5/4076* (2013.01); *A61B 5/4094* (2013.01); *A61B 5/4836* (2013.01); *A61B 5/6865* (2013.01); *A61B 5/6868* (2013.01); *A61B 5/6882* (2013.01); *A61B 17/1695* (2013.01); *A61N 1/0539* (2013.01); *A61N 1/36064* (2013.01); *A61N 1/36139* (2013.01); *A61N 1/0531* (2013.01)

(58) Field of Classification Search
USPC .......................................................... 607/45
See application file for complete search history.

(56) References Cited

U.S. PATENT DOCUMENTS

| | | | |
|---|---|---|---|
| 5,865,842 A | 2/1999 | Knuth et al. | |
| 5,938,689 A | 8/1999 | Fischell et al. | |
| 6,011,991 A | 1/2000 | Mardirossian | |
| 6,016,449 A | 1/2000 | Fischell et al. | |
| 6,051,017 A | 4/2000 | Loeb et al. | |
| 6,175,764 B1 | 1/2001 | Loeb et al. | |
| 6,181,965 B1 | 1/2001 | Loeb et al. | |
| 6,185,452 B1 | 2/2001 | Schulman et al. | |
| 6,208,894 B1 | 3/2001 | Schulman et al. | |
| 6,240,316 B1 | 5/2001 | Richmond et al. | |
| 6,427,086 B1 | 7/2002 | Fischell et al. | |
| 6,482,182 B1 | 11/2002 | Carroll et al. | |
| 6,493,592 B1 | 12/2002 | Leonard et al. | |
| 6,546,277 B1 | 4/2003 | Franck et al. | |
| 6,549,810 B1 | 4/2003 | Leonard et al. | |
| 6,582,441 B1 | 6/2003 | He et al. | |
| 6,597,954 B1 | 7/2003 | Fischell et al. | |
| 6,622,051 B1 | 9/2003 | Bishay et al. | |
| 6,623,490 B1 | 9/2003 | Crane et al. | |
| 6,711,430 B1 | 3/2004 | Ferris et al. | |
| 6,731,976 B2 | 5/2004 | Penn et al. | |
| 6,735,475 B1 | 5/2004 | Whitehurst et al. | |
| 6,782,292 B2 | 8/2004 | Whitehurst | |
| 6,788,975 B1 | 9/2004 | Whitehurst et al. | |
| 6,795,737 B2 | 9/2004 | Gielen et al. | |
| 6,819,956 B2 | 11/2004 | DiLorenzo | |
| 6,830,544 B2 | 12/2004 | Tanner | |
| 6,862,479 B1 | 3/2005 | Whitehurst et al. | |
| 6,871,098 B2 | 3/2005 | Nuttin | |
| 6,922,590 B1 | 7/2005 | Whitehurst | |
| 6,950,707 B2 | 9/2005 | Whitehurst | |
| 6,959,215 B2 | 10/2005 | Gliner et al. | |
| 6,970,741 B1 | 11/2005 | Whitehurst et al. | |
| 6,990,377 B2 | 1/2006 | Gliner et al. | |
| 7,003,352 B1 | 2/2006 | Whitehurst | |
| 7,006,859 B1 | 2/2006 | Osorio et al. | |
| 7,013,177 B1 | 3/2006 | Whitehurst et al. | |
| 7,063,708 B2 | 6/2006 | Gibson et al. | |
| 7,103,408 B2 | 9/2006 | Haller et al. | |
| 7,107,103 B2 | 9/2006 | Schulman et al. | |
| 7,146,217 B2 | 12/2006 | Firlik et al. | |
| 7,151,961 B1 | 12/2006 | Whitehurst et al. | |
| 7,158,333 B1 | 1/2007 | Sutardja et al. | |
| 7,167,751 B1 | 1/2007 | Whitehurst et al. | |
| 7,174,212 B1 | 2/2007 | Klehn et al. | |
| 7,187,967 B2 | 3/2007 | Kennedy | |
| 7,209,787 B2 | 4/2007 | DiLorenzo | |
| 7,221,981 B2 | 5/2007 | Gliner | |
| 7,236,830 B2 | 6/2007 | Gliner | |
| 7,236,831 B2 | 6/2007 | Firlik et al. | |
| 7,255,686 B2 | 8/2007 | Putz | |
| 7,283,856 B2 | 10/2007 | Boling | |
| 7,292,890 B2 | 11/2007 | Whitehurst et al. | |
| 7,299,096 B2 | 11/2007 | Balzer et al. | |
| 7,302,298 B2 | 11/2007 | Lowry et al. | |
| 7,305,268 B2 | 12/2007 | Gliner et al. | |
| D565,735 S | 4/2008 | Washbon | |
| 7,353,064 B2 | 4/2008 | Gliner et al. | |
| 7,376,468 B2 | 5/2008 | King et al. | |
| 7,406,105 B2 | 7/2008 | DelMain et al. | |
| 7,604,658 B2 | 10/2009 | Wilson et al. | |
| 7,937,160 B2 | 5/2011 | Garabedian et al. | |
| 9,179,875 B2 * | 11/2015 | Hua .................... A61B 5/6865 |
| 2001/0003156 A1 | 6/2001 | Gill | |
| 2002/0151770 A1 | 10/2002 | Noll, III et al. | |
| 2003/0040753 A1 | 2/2003 | Daum et al. | |
| 2003/0093129 A1 | 5/2003 | Nicolelis et al. | |
| 2003/0233125 A1 | 12/2003 | Kaplan et al. | |
| 2003/0233126 A1 | 12/2003 | Kaplan et al. | |
| 2004/0030236 A1 | 2/2004 | Mazzocchi et al. | |
| 2004/0088024 A1 | 5/2004 | Firlik et al. | |
| 2004/0186532 A1 | 9/2004 | Tadlock | |
| 2004/0225335 A1 | 11/2004 | Whitehurst et al. | |
| 2004/0243130 A1 | 12/2004 | Biscup | |
| 2004/0243207 A1 | 12/2004 | Olson et al. | |
| 2005/0021103 A1 | 1/2005 | Dilorenzo | |
| 2005/0075680 A1 | 4/2005 | Lowry et al. | |
| 2005/0102006 A1 | 5/2005 | Whitehurst et al. | |
| 2005/0131311 A1 | 6/2005 | Leuthardt et al. | |
| 2005/0137652 A1 | 6/2005 | Cauller et al. | |
| 2005/0182453 A1 | 8/2005 | Whitehurst et al. | |
| 2005/0228249 A1 | 10/2005 | Boling | |
| 2005/0245969 A1 | 11/2005 | Loeb | |
| 2005/0251144 A1 | 11/2005 | Wilson et al. | |
| 2005/0251237 A1 | 11/2005 | Kuzma et al. | |
| 2005/0283203 A1 | 12/2005 | Flaherty et al. | |
| 2006/0005845 A1 | 1/2006 | Karr et al. | |
| 2006/0111767 A1 | 5/2006 | Olson et al. | |
| 2006/0129203 A1 | 6/2006 | Garabedian et al. | |
| 2006/0173522 A1 | 8/2006 | Osorio | |
| 2006/0184143 A1 | 8/2006 | Jolly et al. | |
| 2006/0195154 A1 | 8/2006 | Jaax et al. | |
| 2006/0206165 A1 | 9/2006 | Jaax et al. | |
| 2006/0212087 A1 | 9/2006 | Haller et al. | |
| 2006/0212090 A1 | 9/2006 | Lozano et al. | |
| 2006/0212091 A1 | 9/2006 | Lozano et al. | |
| 2006/0241717 A1 | 10/2006 | Whitehurst et al. | |
| 2007/0021800 A1 | 1/2007 | Whitehurst et al. | |
| 2007/0032718 A1 | 2/2007 | Shults et al. | |
| 2007/0032839 A1 | 2/2007 | Parramon et al. | |
| 2007/0100393 A1 | 5/2007 | Whitehurst et al. | |
| 2007/0106143 A1 | 5/2007 | Flaherty | |
| 2007/0123954 A1 | 5/2007 | Gielen et al. | |
| 2007/0135867 A1 | 6/2007 | Klosterman et al. | |
| 2007/0173733 A1 | 7/2007 | Le et al. | |
| 2007/0233158 A1 | 10/2007 | Rodriguez | |
| 2007/0265582 A1 | 11/2007 | Kaplan et al. | |
| 2007/0282395 A1 | 12/2007 | Mal tan et al. | |
| 2007/0282396 A1 | 12/2007 | Overstreet et al. | |
| 2008/0004676 A1 | 1/2008 | Osypka et al. | |
| 2008/0009920 A1 | 1/2008 | Gibson et al. | |
| 2008/0071323 A1 | 3/2008 | Lowry et al. | |
| 2008/0097519 A1 | 4/2008 | Calderon et al. | |
| 2008/0140154 A1 | 6/2008 | Loeb et al. | |
| 2008/0183241 A1 | 7/2008 | Bedenbaugh | |
| 2008/0208074 A1 | 8/2008 | Snyder et al. | |
| 2008/0208302 A1 | 8/2008 | Alexander et al. | |
| 2008/0218472 A1 | 9/2008 | Breen et al. | |
| 2008/0312716 A1 | 12/2008 | Russell | |
| 2009/0018599 A1 | 1/2009 | Hastings et al. | |
| 2009/0112278 A1 | 4/2009 | Wingeier et al. | |
| 2009/0118804 A1 | 5/2009 | Moffitt et al. | |

(56) References Cited

U.S. PATENT DOCUMENTS

2009/0259137 A1 10/2009 Delic et al.
2014/0194720 A1 7/2014 Hua

FOREIGN PATENT DOCUMENTS

| JP | 10-080431 | 3/1998 |
| --- | --- | --- |
| JP | 2005-516697 | 6/2005 |
| JP | 2005-5166975 | 6/2005 |
| JP | 2005-324017 | 11/2005 |
| JP | 2006-518655 | 8/2006 |
| JP | 2007-524463 | 8/2007 |
| WO | WO 03/066153 | 8/2003 |
| WO | WO 2004/075768 | 9/2004 |
| WO | WO 2006/019723 | 2/2006 |
| WO | WO 2010/085782 | 7/2010 |
| WO | WO 2011/084788 | 7/2011 |

OTHER PUBLICATIONS

Notification of Transmittal of International Preliminary Report on Patentability, dated Jul. 5, 2012, PCT/US2010/061531.

European Patent Office; European Search Report of Related European Application No. 10842715.4; Search Report Issue Date Jun. 6, 2013.

Chinese Office Action dated Feb. 14, 2014, from CN Patent Application No. 201080058486.4.

Chinese Search Report dated Jan. 15, 2014, from CN Patent Application No. 201080058486.4.

Carbunaru, R. et al., "Rechargeable Battery-Powered bion® Microstimulators for Neuromodulation," Proceedings of the 26th Annual International Conference of the IEEE EMBS San Francisco, CA, USA, Sep. 1-5, 2004. 0-7803-B439-3/04/$20.00 © 2004 IEEE.

Giles, Jim, "Electric currents boosts brain power" in Nature, Oct. 26, 2004.

Loeb, Gerald E. et al., "The Bion Devices: Injectable Interfaces With Peripheral Nerves and Muscles." Neurosurg Focus. 2006;20(5) ©2006 American Association of Neurological Surgeons Posted Aug. 15, 2006.

Simonite, Tim. "Brain blanket boosts mind control" in New Scientist. Feb. 15, 2008, posted online.

Singer, Emily, "Want to Enhance Your Brain Power? Research hints that electrically stimulating the brain can speed learning," MIT Technology Review, Jun. 26, 2008.

International Search Report and Written Opinion, dated Sep. 8, 2011, from International Application No. PCT/US2010/061531.

* cited by examiner

1A

1B

5A

5B

6A

6B

6C

7A

7B

7C

7D

7E 8A    8B

8C

10A

10B

10C

10D

INSERTION OF MEDICAL DEVICES THROUGH NON-ORTHOGONAL AND ORTHOGONAL TRAJECTORIES WITHIN THE CRANIUM AND METHODS OF USING

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation application of U.S. application Ser. No. 13/318,462, filed Nov. 1, 2011, now U.S. Pat. No. 9,179,875, issued Nov. 10, 2015, which is a National Phase Application of PCT International Application No. PCT/US2010/061531, filed Dec. 21, 2010, which claims priority benefit of U.S. Provisional Application No. 61/288,619, filed Dec. 21, 2009, the entirety of each which is hereby incorporated by reference herein.

BACKGROUND

Field

The present invention relates to medical devices, systems and methods for accessing cranial and intracranial structures. Specifically, the invention is directed to altering brain function and treating cranial and intracranial pathology. More specifically, the invention is directed to the surgical implantation of electrodes or other devices within or through the cranium to alter or improve brain function and pathological states such as stroke, seizure, degeneration, and brain tumors. Most specifically, the invention is directed to minimizing surgical methods and risks and maximizing the length of devices that can be implanted within or through the cranium and their ability to hold charge.

Description of the Related Art

Electrical stimulation of the brain can improve and ameliorate many neurologic conditions. Examples of the success of brain stimulation include deep brain stimulation for Parkinson's Disease, tremor, dystonia, other movement disorders, epilepsy, and pain. Additionally, potential new sites of deep brain stimulation demonstrate promising results for other conditions such as obesity, depression, psychiatric disorders, memory, migraine headache, and minimally conscious states.

Deep brain stimulation involves placing a long electrode through a burrhole in the cranium to a target deep to the surface of the brain. The electrode is placed under stereotactic guidance which is performed with or without a frame. Frame based systems such as the Leksell frame require that a rigid stereotactic frame is clamped to the skull through a number of screws that are fixed to the cranium. Frameless systems utilize fiducial markers placed on the skin. In both methods, an MRI (magnetic resonance imaging) or CT (computed tomography) scan is performed with the frame or fiducial markers in place. In frame based stereotaxy, computer assisted reconstruction of the brain and target area is performed to localize the target in relation to the coordinates of the frame. In frameless stereotaxy, a three-dimensional reconstruction of the cranium and brain is matched to the three-dimensional configuration of the fiducial markers. The end result in both cases is the ability to place electrodes accurately into virtually any part of the brain.

The cerebral cortex is another structure that yields a large potential for therapeutic intervention. In deep brain stimulation, the electrode passes through the cerebral cortex as well as subcortical brain structures to reach the affected deep brain nuclei and therefore risks injury to the intervening healthy brain tissues as well as blood vessels. These unnecessary yet unavoidable injuries can potentially result in loss of brain functions, stroke, and intracranial hemorrhage. On the other hand, stimulation of the cerebral cortex is safer because electrodes are placed on the surface of the brain or even outside the covering of the brain, i.e. dura mater, a technique called epidural electrode stimulation. Additionally most of the subcortical or deep brain structures have connections with known targets in the cortex, making these targets candidates for cortical stimulation. Accordingly, directly stimulating the cortex can affect subcortical and deep brain structures that directly or indirectly communicate with the cortical targets. Previous studies have demonstrated success in using cortical stimulation for the treatment of epilepsy, stroke rehabilitation, pain, depression, and blindness.

In addition to the treatment of pathologic conditions, brain stimulation and recording provides the virtually unlimited potential of augmenting or improving brain function. These technologies allow the brain to bypass dysfunctional neural elements such as due to spinal cord injury, amyotrophic lateral sclerosis (ALS), stroke, multiple sclerosis (MS), and blindness. Brain recording and stimulation techniques in these cases provide a bridge for neural signals to cross injured or dysfunctional elements both on the input as well as the output side. For example in the case of ALS or a patient with locked-in syndrome, the patient is awake and conscious but without any ability to interact with the environment. These patients are essentially trapped within their brain. Recently, it has been demonstrated that by placing recording electrodes directly on the surface of the brain, these patients can learn to control computer cursors and other devices through their own brainwaves. This method of direct control of external devices through brainwaves is called brain-machine interface Brain-machine interface has also been implemented using brainwaves recorded outside the cranium—electroencephalography (EEG), which detects the neural signals passing through the cranium with electrodes placed on the scalp. Although noninvasive, brain-machine interface using EEG signals is currently limited from the significant dampening of the brainwave's amplitude by the cranium. Only the largest potentials among the brain signals are detectable by the EEG approach.

Similarly the cortex and some subcortical fibers can be activated through the cranium by transcranial magnetic stimulation (TMS) or transcranial direct current stimulation (tDCS). In this approach, magnetic waves (TMS) or electrical currents (tDCS) are activated on the scalp outside the cranium and transmitted through the cranium to activate parts of the cortex and subcortical fibers. TMS has been effective in treating a number of disorders such as depression, migraines, and movement disorders. Additionally some reports suggest that TMS may be able to boost memory and concentration. Similarly tDCS appears to improve some forms of learning when applied in low doses. This evidence suggests that stimulation of the cortex may have a large, virtually unlimited, variety of applications for treating central nervous system pathology as well as enhancing normal brain functions.

Electrical stimulation has also been applied effectively for the treatment of certain tumors. By applying an electrical field that disrupts the physiology of tumor cells, tumors have been found to shrink. Tumors in the brain, particularly those close to the surface of the brain such as meningiomas may also be treated by electrical stimulation. In addition to electrical fields, heat (thermoablation) and cold (cryoablation) have also demonstrated effectiveness towards tumors.

Prior art and current state of the art for brain stimulation technologies require the placement of electrodes either through a craniotomy where a flap of the skull is removed and then replaced, or a burr hole where a small hole is drilled in the skull and the brain can be visualized. These procedures necessitate a minimum of an overnight stay in the hospital and pose risk to injury of the brain due to the invasiveness of the techniques. Additionally these "open" techniques pose special challenges for securing the electrode as most technologies require a lead to exit the hole in the skull. Unless these electrodes are tethered by a suture or device, there is possibility of migration or movement, particularly in the context of continuous pulsatile movement of the brain in relation to the skull.

Current techniques for cortical stimulation also risk the development of scarring of the cortex as well as hemorrhage. With long term placement of foreign objects on the brain or spine, scarring (gliosis and inflammation) occurs. This is seen with both spinal cord stimulators placed on the spinal cord as well as prostheses placed on the surface of the brain. Scarring distorts the normal brain architecture and may lead to complications such as seizures. Additionally, the placement of devices on the surface of the brain poses risks of hemorrhage. A previous clinical case illustrates the dangers: a patient who received subdural cortical electrode implantation suffered significant intracranial hemorrhage after suffering head trauma. Thus in the case of a deceleration injury like that seen in traffic accidents or falls, the imperfect anchoring of the electrode and the mass of the electode may cause the electrodes to detach and injure the brain. Blood vessels also can be sheared from the sudden relative movement of the electrode on the brain, leading to subdural, subarachnoid, and cortical hematomas. However, if the electrodes were embedded within the skull then there is no risk of this type of shearing injury during traumatic brain injury such as from sudden impact accidents.

In order to expand the indications of brain stimulation to a larger population of patients, the invasiveness of techniques for placement of the electrodes needs to be minimized. As many surgical specialties have demonstrated, minimized surgical approaches often translate into safer surgeries with shorter hospital stays and greater patient satisfaction.

Recent advances in the miniaturization of microelectronics have allowed the development of small, completely contained electrode systems, called the bion, that are small enough to be injected into muscle and other body parts through a syringe. This type of microelectrode device contains stimulation and recording electrodes, amplifier, communication, and power components all integrated into a hermetically sealed capsule. While some bion devices have batteries integrated with the unit, others are powered by radiofrequency transmission. Although muscle and other body parts allow the implantation of bion electrodes, the cranium poses a challenge to the bion because the cranium is roughly 1 cm or less in thickness. This finite thickness limits the size of the electronic components as well as the size of the battery. Battery capacity (the amount of energy stored within the battery) determines the length of time between charges in a rechargeable battery and is effected by the length of the battery. In the case of the bion, an injectable device that demands a small diameter, the battery capacity is directly related to the length of the battery. A longer bion electrode permits a longer battery and hence greater battery capacity and a longer run time without recharging.

Some patents exist covering implantable stimulators and electrical stimulation therapy systems. However, these patents are not specially adapted for insertion through the skull with multiple components through a single site by means of introducing some components at non-orthogonal angles.

In the present invention an electrode can communicate with and work together with other electrodes and supporting components (i.e. receivers, transmitters, batteries, rechargers, etc.) for an integrated therapy system with multiple components insertable through the same

SUMMARY

The invention involves an improved method of implanting effectors, sensors, systems of effectors and sensors, and other implantable medical devices into the body through skin, bone, muscle, tissue, and other intermediary material between an external surface of the body and the intended physical contact. The physical contact within the body may be the target from which information is gathered with the sensors or to which energy is directed with the effectors. Alternatively, the physical contact may be a transceiver station from which information is received by the sensor from another target (deeper inside) or from which energy is sent by the effectors to another target (deeper inside). When implanted into the cranium the devices of the present invention described herein are referred to as a Cranion™.

The effector may include any component that produces or induces an effect or acts as a stimulus at a target within the body. A preferred example of an effector is an electrode producing an effect through electricity. Other types of effectors produce effects using magnetism, temperature, infrared radiation, light, vibrations, hypersonic energy (frequencies above human hearing), ultrasonic energy, radiowaves, microwaves, etc. and include transmitters of these other forms of energy.

The sensor may receive and record data relating to temperature, light, density, impedance, etc., in the form of radiowaves, microwaves, spectroscopy, etc.

According to a preferred embodiment, the invention focuses on improved devices and methods for implantation through the cranium to provide brain therapy and therapeutic treatment of medical conditions having a neurological component.

The improved method involves modification of implantable devices to specific sizes and shapes so that one or several can be inserted simultaneously through a single entry site in the cranium by altering the insertion angle of each unit. The individual units are inserted orthogonally and/or nonorthogonally relative to the surface of the cranium tangent to the singular common entry site. The individual units may be physically connected through a connector head at the common entry site, thereby sharing electronics, power, and other attributes. Additionally, in some embodiments, the distal tip of the shaft and the shaft of the device may be configured so that the devices are insertable directly. By insertable directly it is meant that no or few other tools or instruments are needed to make the entry site and/or the hole through which the implanted device is inserted. For example, the device may be encapsulated in a helical externally threaded screw housing such that the shaft has a sharp distal tip allowing the whole device to pierce through the skin and screw into bone similar to currently used self-drilling cranial plating screws. The self-inserting characteristic enables electrodes to be inserted almost anywhere very quickly in a minimally invasive screw-in or pop-in procedure.

The types of medical devices that can be modified and implanted by the methods described in this invention are virtually unlimited and include neural stimulation systems, neural recording systems, brain machine interface systems, cryotherapy systems, thermotherapy systems, magnetic field generating systems, radiation emitting systems, auditory systems, iontophoresis systems, interpersonal communication systems, interorganism communication systems, et al. Currently, electrodes placed on or near the surface of the brain have been used clinically to treat a number of disorders including seizures, pain syndromes, movement disorders, psychiatric disorders, paralysis, and neurodegenerative disorders like ALS. One preferred embodiment of the invention is to implant one or more cortical stimulation and recording electrodes close to the surface of the cortex through a single minimally invasive cranial entry site while enhancing the battery life and complexity of each electrode unit by allowing each unit to be greater in size (particularly length) than the thickness of the skull since they are adapted for insertion at an oblique angle and not limited to perpendicular insertion. However, consistent with the present invention, some electrodes (or other effectors) can be also be equal to or shorter than the thickness of the skull. Multicomponent devices and systems of devices with shorter electrodes (or other components) adapted for insertion of shafts at a variety of angles permits more components than previously possible through a single entry site. The electrodes may take the form of an implantable microstimulator or improved bion that is embedded in the skull with its tip placed either epidurally (upon the dura mater) or subdurally (below the dura mater) near the surface of the brain.

The thickness of the cranium is limited to a length of 5 mm to 10 mm. If electrodes are inserted straight down, perpendicular (orthogonal) to the surface of the cranium, their lengths would be limited to a maximum of approximately 1 cm. Electrodes longer than 1 cm that are implanted in the cranium orthogonally would protrude through the skull into the brain. Placement of electrodes into brain substance increases the risk of injury to brain and blood vessels both during the time of placement as well as afterwards given the physiologic pulsation of the brain in relation to the cranium as well as during episodes of head trauma which causes acceleration and deceleration movement of the brain in relation to the cranium. Current methods of cortical stimulation place electrodes either epidurally (outside the dura mater) or subdurally (in between the dura mater and arachnoid or epi-arachnoid). Placement of electrodes in either of these locations provides for low impedance stimulation of the brain while maximizing safety. Current methods of placement of cortical electrodes necessitates drilling of a burr hole or craniotomy, both of which pose risks to the patient and commonly require a stay in the intensive care unit to monitor postoperatively.

The current invention describes the method of insertion of devices and electrode units through orthogonal and nonorthogonal trajectories through the cranium. Angled insertion of the electrode units enables longer units (length greater than skull thickness) to be used without penetrating into the brain. The angled electrodes pass almost entirely through the skull and then just barely protrude towards cerebral cortex. Longer electrodes units are desirable because the length of a battery is proportional to the size and capacity of the battery. Thus longer electrode units can contain longer and larger batteries. Preferably, the batteries are rechargeable. However, regardless of whether the batteries are rechargeable, it is desirable for the stimulation electrodes to have a maximum battery capacity (time until replacement or recharging). Higher capacity batteries provide sustained therapy and enhance patient mobility and freedom. The greater mobility and freedom provided by higher capacity batteries in longer electrodes increases the probability of patient compliance for out-patient procedures because it is easier to comply with prescribed therapeutic regimens while living a normal life.

Longer electrodes units also allow more components to be integrated within each implant. Larger size allows flexibility in terms of the complexity of the circuitry, communication components, as well as the inclusion of both recording (receiving) and stimulation (transmitting) capabilities. Additionally, multiple electrode contacts can be placed within a single implant with greater ease, i.e. bipolar, tripolar, tetrapolar stimulation or recording within each electrode unit.

The ability to insert several electrodes units through a single cranial entry site is highly advantageous. The cranium obviously provides an important protective function for the brain. Accordingly, it is desirable to keep the cranium as intact as possible while accessing the brain for therapy. Fewer entry sites in the cranium preserve its integrity and reduce the likelihood of the brain inadvertently being exposed or harmed. However, if fewer entry sites imply fewer electrodes this may have drawbacks with respect to the variety and intensity of therapy that can be provided. The ability to insert several electrodes through a single site provides powerful therapy without jeopardizing the cranium and more importantly, the brain and blood vessels beneath. When more intense therapy is not needed, multiple electrodes in the same region may still have advantages because they can be selectively, individually activated to prolong the time until recharging. For example, with electrodes radiating outward in a circle from a common insertion point, when the battery of the first electrode dies the system can automatically or manually advance to turn on the next electrode for it to begin stimulation. Additionally multiple electrodes positioned in a spatially dispersed pattern in two or three dimensional space allows the stimulating current to be steered in that space. Current steering has been utilized in spinal cord stimulation and is performed by differential activation of spatially distinct electrodes. Different electrodes or other components (i.e. sensors) inserted through a common entry site may also be used to provide different therapeutic benefits (electrical stimulation, magnetic stimulation, drug delivery, etc.) or to gather different types of data (blood glucose level, temperature, pH, etc.).

The stimulation module is designed as either a single implant in a single trajectory or multiple implants with multiple trajectories. Depending on the specific need of the individual, the stimulation module may contain one, a combination, or all of the following components: stimulation electrode(s), recording electrode(s), pulse generator, system control unit, battery, capacitor, current sink, data signal transmitter, data signal receiver, receiver coil, transceiver, transducer, sensors, program storage, memory unit, internal electronics, analysis circuitry or software, etc. All of these components can be contained within a single implant similar to a bion. However, these components can also be broken down into separate units that are implanted in separate trajectories. Because the units pass through a single entry site, they can be hard wired at this point. Optionally, they may communicate wirelessly with each other. For example, if an individual wanted or needed an implant with a longer battery life, then multiple units composed of batteries can be implanted and wired together. Since the battery units do not need to contain an electrode or pass through the inner table of the skull, battery units can be implanted in a trajectory with the maximum length permitted by the curvature of the cancellous portion of the cranium without passing through the inner or outer cortical layers of the cranium. Non-rigid units that curve with the curvature of the cranium permit even longer implants. These curved electrodes can slide into the cancellous skull trapped in between the inner and outer cortical layers. The curved stimulators and electrodes do not have to be stiff or rigid but can be semi-flexible to more easily slide into and maneuver within the cancellous space. In fact only the actual electrode contacts need to pass through the cranium into the epidural or subdural space. All other components can be implanted within the cranium without exiting the cranium. This system is customized with the modules or components specific for each individual, each brain target, and each specific purpose or disorder that is being treated.

The implantable stimulating electrodes and associated components provided herein have a plethora of uses. In addition to existing applications of neuromodulation in Parkinson's Disease and epilepsy, they can be used to stimulate a healthy, normal brain to enhance memory, accelerate learning, etc. (See Singer, Emily, "Want to Enhance Your Brain Power? Research hints that electrically stimulating the brain can speed learning", MIT Technology Review, Jun. 26, 2008; and Giles, Jim, "Electric current boosts brain power" in Nature, Oct. 26, 2004.) They can also be used on a damaged brain to stimulate regeneration, repair as well as to record changes to enable a patient (including non-human patients such as animals) to communicate with the outside world simply by using their brain. This offers hope for patients with paralysis after stroke, spinal cord injury or other disorders (ALS, polio, etc). Another application is to use the implantable cranial electrode as means for brainwave communication between people or other living organisms so that with training, one person (or other living organism, including other animals and potentially plants) can learn to recognize specific patterns of neural signals from another. In this manner it may be possible for people and other living organisms to have invisible, inaudible conversations using only their thoughts and brain waves. This technology has important commercial as well as military applications. Additionally implantable units do not have to access the brain for communication; instead, vibrations generated by implants positioned elsewhere can directly stimulate the inner ear for communication. For example, the stimulator (with multiple components at multiple angles through a single site) may be used as a transmitter and receiver in the inner ear with the capacity to interact with a cell phone (such as via Bluetooth technology) for hands free conversation. Related ear devices have shown success when used in partially deaf people (or other animals) to transmit auditory signals to the opposite ear as in cases of outer ear or one-sided deafness.

Although electrode stimulation and recording has a wide potential of uses mirroring those currently in use clinically, other preferred embodiments are plentiful. Another preferred embodiment is an implant that uses temperature differences to activate or deactivate the brain or intracranial tissue. In this embodiment, the heat conducive element is implanted through the cranium into the subdural or epidural space. The components that are implanted through other trajectories include those described in the electrode embodiment described above, but also include heat pumps, thermogenerators, and thermoregulators. Cooling the brain typically deactivates the neural activity and can be utilized for seizures, migraines, pain, and other disorders.

The electronic circuitry of the present invention is amenable to various configurations or embodiments. The invention covers the electronic circuitry configurations of any conventional electrodes, stimulators, bions, etc. adapted for insertion of multiple components transversely through the cranium at orthogonal and/or non-orthogonal angles.

Other objectives and advantages of the invention will be set forth in the description which follows. Implicit modifications of the present invention based on the explicit descriptions will be, at least in part, obvious from the description, or may be learned by practice of the invention. Such subtle, predictable modifications and adaptations are taken to be within the scope of the present invention. Additional advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1A shows two non-orthogonal trajectories both of which have the same axial angle ($\theta_1$) with respect to the perpendicular axis at the entry site. The radial angle ($\theta_2$) is the angle on the tangent plane to the skin or skull at the entry site. For convention anatomic anterior orientation, i.e. the direction towards the front of the face, or the component of the anterior orientation projected onto the tangent plane at the entry site is taken as zero degrees.

FIG. 5A shows that a thinner device with smaller diameter can have greater length with greater axial angle of insertion ($\theta_1$). However when the device has a diameter similar to the thickness of the skull, as shown in (B), the length of the device cannot change with any axial angle of insertion ($\theta_1$). FIG. 5B also shows that as the axial angle increases, the tip of the larger diameter device is no longer able to penetrate the inner cortical layer of the skull. Instead the side of the device penetrates the inner cortex. In contrast, (A) demonstrates that a thinner device is still able to penetrate the inner cortex with the tip at greater axial angles ($\theta_1$). Thus in general, non-orthogonal insertion of devices requires that the width or diameter of the device be less than the thickness of the skull.

FIG. 6A. shows an broad top view while (B) shows a side view, and (C) shows a view from inside the cranium. A single small burr hole is used to insert all four shafts. The single burr hole is of partial thickness because the edges at the bottom of the partial burr hole are used to guide the tips of the self-drilling shafts or drill bits. Two longer shafts flank two shorter shafts resulting in a linear array as seen in (C) where four tips of the shafts are seen protruding through the inner cortex. A linear array of stimulation as shown in FIG. 6 is useful for stimulation along a linear gyms such as for motor cortex stimulation, where typically a small craniotomy is used to place a strip electrode.

FIG. 8A. shows the drilling of a non-orthogonal hole through the cranium by a self-drilling shaft. In (B), an inner compartment of the shaft is unlocked and removed from the outer threaded portion, leaving a cylindrical conduit. This conduit allows one or more electrode arrays to be inserted into the epidural or subdural space (C). The angled, non-orthogonal trajectory of the shaft allows the electrode array to safely slide into the epidural or subdural space at a shallow angle. In contrast if the burr hole were orthogonally oriented, the electrode array would have to make a 90 degree turn after passing through the skull. The electrode array can be directed similarly to spinal cord stimulation electrode array using mechanical turning by a small bend in the distal tip of the inner stylet. Alternatively, the distal inner cannular may be ferromagnetic allowing an external magnetic or electromagnetic field to guide or direct the tip of the electrode array. Lastly, a fibroptic inner cannula with distal camera would allow endoscopic guidance of the electrode array under direct visualization of epidural, subdural, or intraventricular structures. The tip of the stylet also would allow for stereotactic image guidance by emitting signals such as radiofrequency or sonic/ultrasonic impulses that help localize the distal tip in stereotactic coordinates. Once the target and desired placement of the electrode array has been accomplished, the proximal end is secured to the cranial conduit/shaft by a locking mechanism. Alternatively, other components such as a battery, controller, transducer, etc. can also be placed inside the cannula, or in other trajectories through the cranium from the same entry site. The combination of multiple shaft placement through a single entry site with multiple steerable electrode arrays allow a limitless configuration of brain stimulation and recording through a single small burr hole.

FIG. 10A. shows the empty head unit with three docking stations. FIG. 10B shows the insertion of a single shaft into one docking station. Two shafts are inserted into the head unit in (C), while all three shafts have been inserted in (D). The head unit allows direct communication and connection between all shafts and components of the shafts. The head unit itself can also contain multiple components of the overall device such as battery, communication systems, transducers, etc. The head unit can be inserted into a pre made burr hole or be self-inserted by having a self-drilling and self-tapping pointed tip. The head unit does not need to have its own fixation to the skull as the insertion of shafts through the docking stations acts to lock the docking station into the skull. Each docking station can also have adjustable angles of insertion by having a rotating ball and socket mechanism as the docking station through which shafts are inserted.

DETAILED DESCRIPTION

The present invention and method of its use enables multiple effectors, sensors, and other components to fit through a single entry site to provide improved and/or longer-lasting therapeutic benefits. According to some embodiments this is accomplished by inserting the effectors, sensors, other components, or shafts housing any of these elements at different angles to permit greater subsurface reach given a small surface entry site. As used herein, the term "entry site" includes one or more physically distinct openings, holes, or incisions, within close proximity to one another and taking up a relatively small total area of space consistent with minimally invasive surgical procedures. Thus, an "entry site" may be one opening or hole but is not limited to such. The "entry site" may also be an entry zone, area, or region that encompasses two, three, four, or more distinct openings.

Figure 1:
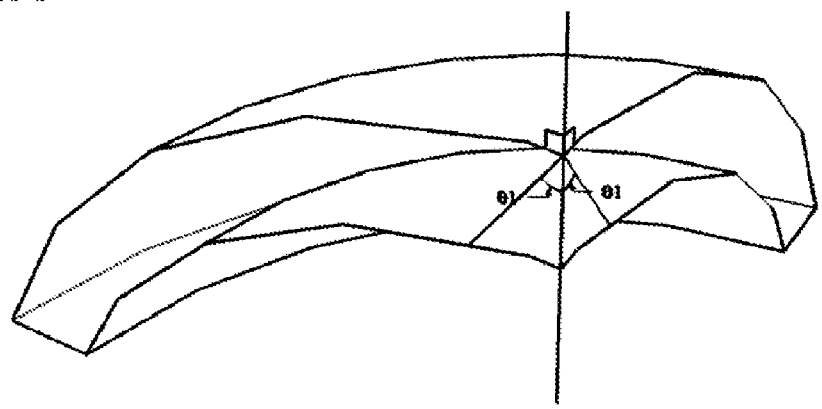
FIG. 1 shows how the trajectory of each device or shaft at a particular entry site is defined by an axial angle ($\theta_1$) (FIG. A) and a radial angle ($\theta_2$) (FIG. B). The skull is represented by a hemi-sphere with 2 cross sections in (A) and 1 cross section in (B).
Figure 1:
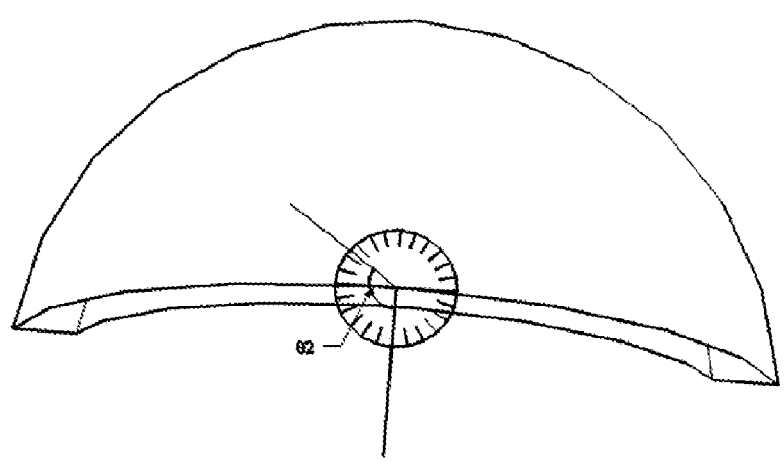

For each entry site, the stimulator/sensor devices may be inserted at several different axial angles between an axis perpendicular to the skin's surface (straight down) and a plane tangent to the skin's surface at the entry site. The effectors (i.e. electrodes) and/or sensors may also be inserted at several different radial angles around the periphery of an entry site in the plane of the tangent to the entry site. The location of the entry site, the axial ($\theta_1$) and the radial ($\theta_2$) insertion angles determine an unique trajectory in the skull and in the body. Preferably, no two stimulator/sensor devices (comprising at least one effector or sensor as part of the device) have the same set of axial ($\theta_1$), radial ($\theta_2$) angles, and entry site location so that each device (and each effector or sensor therein) occupies a unique position different from the others. The closer the first diagonal axial angle is to parallel to the skin surface, the longer the effector or sensor can be while still traversing substantially laterally through the skull without reaching the brain. Conversely, the closer the first diagonal axial angle is to perpendicular to the skin's surface (straight down), the shorter the effector or sensor must be because it is moving more closely to vertical though the skull and is thereby more strictly limited by the skull's vertical thickness. (See FIG. 1.)

Angled implantation allows implantation of extra components to support or work together with the effector or sensor (i.e. electrode) to form a longer-lasting system or improved bion. For example, the main device may be implanted perpendicularly but one or more components (i.e. extended batteries or battery packs) are implanted at an angle. This allows extra components that support a main electrode to be embedded within the skull at an angle. More supporting batteries prolongs the life of the electrode while effectively breaking up the overall implant into several components that are connected (i.e. at the top) by a connector head or connector. Other components, in addition to batteries, can be transmitters, receivers, radio transceivers, heat generators, cooling devices, magnetic coils, capacitors, transformers, ultrasonic transducers, hypersonic emitters/receivers, electrophysiological recording means, sensors, iontophoresis means, optical stimulators, lasers, cameras, address/positioning units, etc.

As used herein, the term "component" includes effectors and sensors but is not limited to these categories. "Component" might also include other categories of auxiliary, complimentary, or supplementary elements that support an effector or sensor but do not themselves produce an effect on a body or sense (gather data) directly. For example, "component" might include a buffer solution, a physical cushion, a catalyst, a battery, a vacuum line, etc. The present invention includes an implant in which at least one component is an effector or sensor. The implant may also include other additional components that are also effectors or sensors, or are neither effectors nor sensors.

The implantable devices described herein are made of biocompatible materials. In a self-inserting embodiment the devices need to be made of material sufficiently durable and hard to penetrate bone without rupturing. In embodiments that rely on pre-drilling a hole more material options are possible and softer, more flexible materials may be used to encapsulate or house the device. According to a preferred embodiment, at least a portion of the device is made of a semi-permeable material that absorbs some molecules, transmits (flow through) some molecules, elutes some molecules, and blocks some molecules. Such a semi-permeable material may be a mesh with openings (for example, tiny nanopores) therein that optionally also includes key cells or molecules (that provide an auxiliary function) embedded therein on its surface.

According to a preferred embodiment, the effectors are electrodes and supporting components (i.e. transmitters, receivers, etc.) of the present invention are designed to be insertable directly or to insert themselves. By "insert themselves" or "insertable directly" it is meant that the components do not require burr holes to be created in the skull with a drill prior to implant and/or that the components do not require expulsion through an introducer (i.e. needle, cannula, etc.). Self inserted screws of this type are typically classified as self-drilling and self-tapping, in that they do not need a pilot hole nor does the hole need to be tapped to form the threaded tract for a screw. This might be accomplished by the components having distal tips that are sharp or a housing that resembles a screw shaft with threads.

Alternatively, the cranial stimulator devices can be helical in shape such that they wind into the bone in a manner similar to coil anchors for sand volleyball nets. The distal tip of the helix enters into a small hole and the curved tail of the device follows.

When drilling into the skull is necessary such as due to increased resistance from bone making self-tapping screws inadequate, a preferred system and method involves using a balloon along one or more sides of the stimulator device. Drilling often creates a hole that is slightly larger than necessary or imperfect in shape such that there is not a tight fit for the screw. The balloon can be filled with air and or fluid after insertion in a deflated condition to close the gap, reducing the imperfect mating between drill hole and stimulator to provide an improved friction fit that renders the stimulator less susceptible to internal drift/migration. The balloon can also be used proximally above the stimulator to push the electrode contacts on its opposite distal end into closer contact with the surface of the cortex.

If the effectors contain, are coated with, or are associated with magnetic means (i.e. coils, magnetic materials, etc.) they can be used to provide magnetic stimulation therapy in addition to electrical stimulation therapy. Magnetic energy can also be used to recharge the electrical batteries. For example, inserting a magnetic coil inside the skull enables one to carry out local magnetic stimulation ("intracranial magnetic stimulation") with a much lower intensity than that used for transcranial magnetic stimulation which requires a large enough magnetic field to travel through the cranium (resulting in a diminution of signal strength in the process) and also is not localized. The inability to localize therapy, also known as poor selectivity, typically results in overbroad application that may cause damage to unintended surrounding regions and too weak an intensity of treatment at the target site. The ability to localize therapy overcomes both of these drawbacks to systemic application.

In addition to electrical and magnetic stimulation the implantable electrode or components associated with it can be used to generate heat or cold. Heat and cold have been shown to influence brain activity such that they can be used to complement, supplement, or as an alternative to electrical and/or magnetic stimulation.

In addition to electrical and magnetic stimulation the implantable electrode or components associated with it can be used to generate heat or cold. Heat and cold have been shown to influence brain activity such that they can be used to complement, supplement, or as an alternative to electrical and/or magnetic stimulation.

In different embodiments the effector batteries can be recharged inside or outside the body or inside the body through connection to a charging device outside the body. According to a preferred embodiment the effector batteries are recharged inside the body through a naturally occurring means including changes in heat, fluid dynamics, etc. The batteries may include a thermogenerator or thermoelectric generator that uses local heat in situ to generate power. Or, the batteries may include a mechanical power generator that uses natural pulsation of the brain relative to the cranium and changes in cerebrospinal fluid pressure to harness and store energy.

Figure 2:
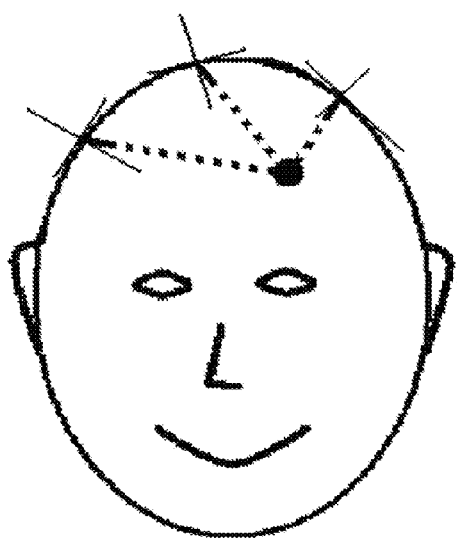
FIG. 2 shows multiple devices from different entry sites, but angled such that they converge on the same target within a brain from different directions.
Figure 3:
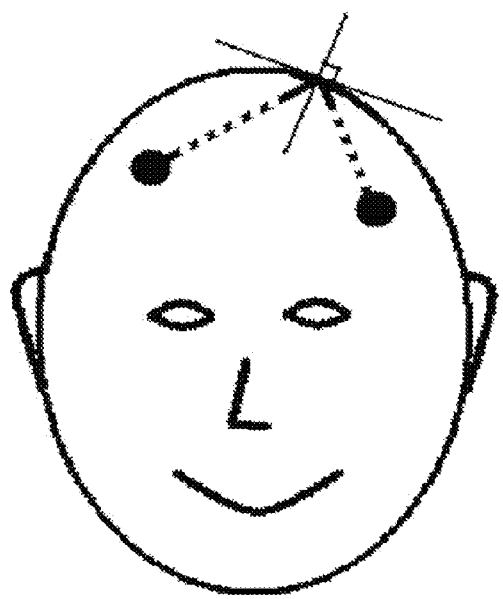
FIG. 3 shows multiple devices inserted from a single entry site at different angles that are divergent from the entry site in order to aim at different targets within a brain.
Figure 4:
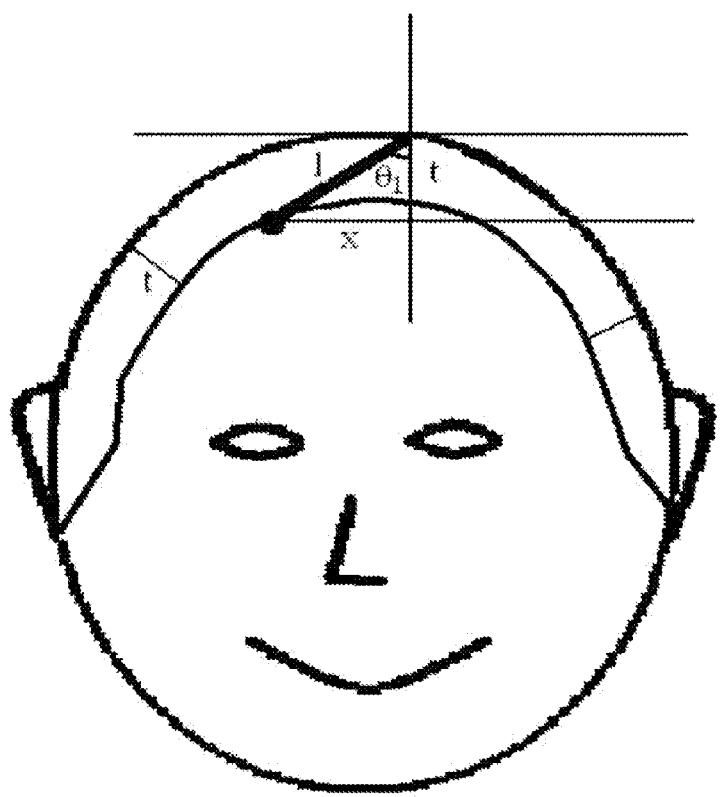
FIG. 4 demonstrates the geometric relationship between the axial angle of device insertion ($\theta_1$) and device length (l) for straight (non-curved devices) that completely traverse a skull thickness (t) based on a lateral displacement variable (x) when the device is fully inserted, $\sin \theta = x/l$.
Figure 5:
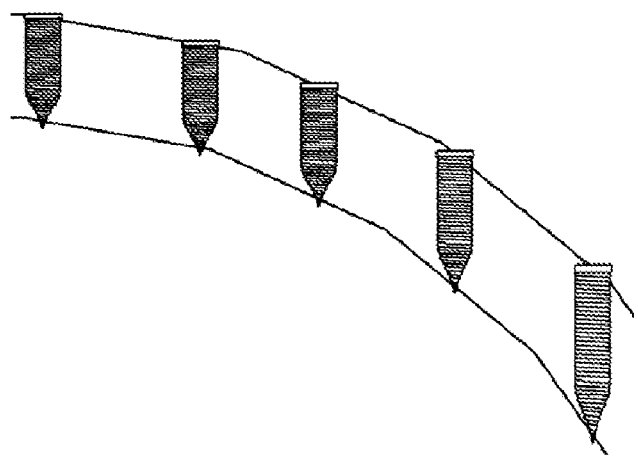
FIG. 5 illustrates the relationship between the thickness or diameter of the device and the maximal length of the device when the device is implanted at an increasingly greater axial angle ($\theta_1$), i.e. greater non-orthogonal insertional angle.
Figure 5:
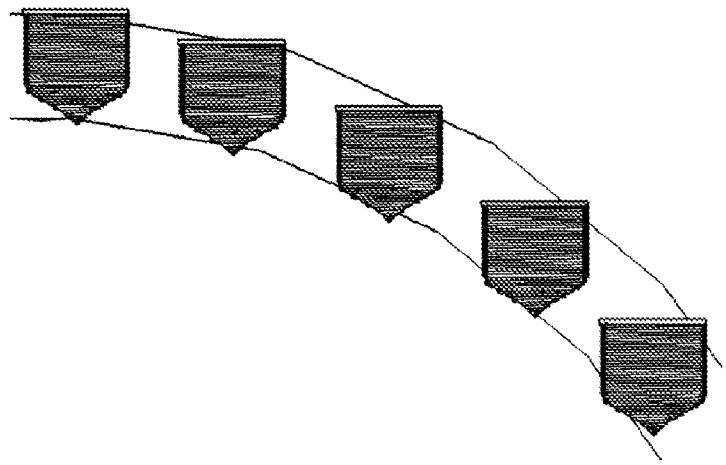
Figure 6:
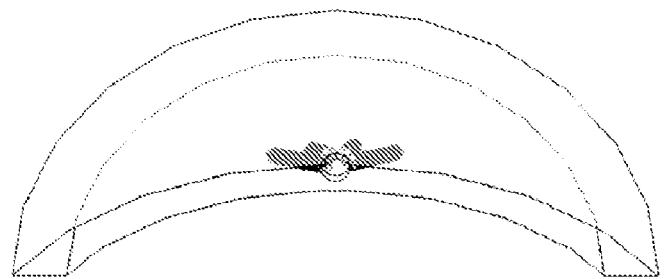
FIG. 6 illustrates a device comprised of four multiple shafts and components arranged in a linear array on the cortex.
Figure 6:
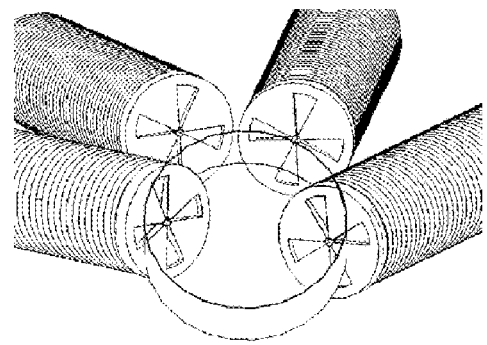
Figure 6:
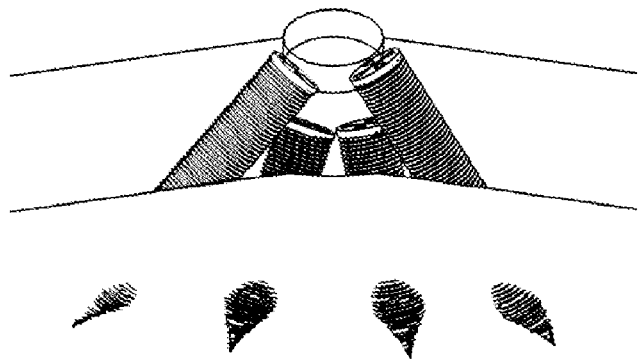

In addition to built-in electrode batteries, the implantable sensor-effector devices of the present invention may be powered by any number of alternative means. In order to reduce their size, they may be powered from outside through a means for receiving energy with the means for receiving energy being smaller than a conventional electrode battery. More specifically, they may rely upon ultrasonic, hypersonic, or radiofrequency energy from a source at another location in the body or outside the body that is absorbed and channeled through a receiving platform. These alternative sources of energy permit the devices to be smaller because a built-in battery is not required. Thus, the device may be made on the scale of microns (length, width, height) rather than millimeters and inserted more deeply into the body, into smaller channels and crevices, or through intact bone and muscle for better accuracy while still being minimally invasive and without sacrificing anatomical structural integrity. Another advantage of the energy source and some of the electronic complexity being outside the body is that it is easier to upgrade and modify from outside. Another advantage of effectors radiating downward and outward from an entry site at different angles is that when a target region for stimulation is deeper within the brain the angle(s) can be set so that rays from more than one effector converge precisely on the deeper target. More than one entry site can be made so that several different devices from several different entry sites converge on the target from different directions (see FIG. 2). Alternatively, when there is more than one target region deep within the brain, effectors from a single entry site can be used to simultaneously reach several different regions by directing the effectors at different angles (see FIG. 3). If the effectors were limited to non-angled, conventional, straight-down insertion all effectors (even through multiple entry sites) would be pointed at the core or center of the brain without the ability to provide targeted therapy to intermediate regions of the brain between the core and the cortex.

In alternative embodiments, the effectors may have additional characteristics that enable them to jointly maximize length and distance within the skull. For example, the effectors may curve with a radius of curvature that approximately matches the radius of curvature or shape of the skull. Since the cranium is composed of three layers, a hard inner cortical layer, a hard outer cortical layer, and a softer cancellous middle layer, long components can be pushed through the cancellous layer being trapped by the harder inner and outer cortical layers. Additionally, the devices may branch out (for example, telescopically) once inserted to form an intracranial pathway that provides additional battery power storage space. However, because the branches would have to traverse through the somewhat hard bone of the cranium these (bifurcated, trifurcated, poly-furcated) embodiments would probably require separate insertion tools capable of drilling worm-like tunnels for the branched devices.

When the effectors are electrodes the circuitry of the present invention for all embodiments is variable. By electronic circuitry it is meant the arrangement and interrelationship between electrodes, batteries, connectors, coils, transmitters, receivers, transceivers, capacitors, controllers/programming means, address means, pulse control means, sensors, etc. Any configuration of these elements that is functional for multiple electrodes inserted transversely through a single entry site (at orthogonal and/or non-orthogonal angles) is consistent with the scope of the present invention.

In other embodiments, the configuration of electronic circuitry is distinctly different in one or more features from conventional products and patent claims, which serves to further distinguish the invention in addition to its other distinguishing features.

As discussed previously, as neurostimulators the devices of the present invention have a myriad of established applications to improve pathologies (movement disorder, psychiatric conditions) and enhance normal functions (learning, memory) in the neural system, particularly through direct interaction with the brain. Additional, potential applications include peripheral nerve stimulation and interaction with other biological systems to catalyze and regulate healing processes. For example, implantable stimulators as described herein may be used at sites of bone fracture or disc degeneration to expedite new bone proliferation as a substitute or supplement to biological or chemical means (bone cement, bone graft, bone filler, bone glue, hydroxyapatite, ground bone composition, or another bone substitute). One specific application is use of stimulators around pedicle screws used in pedicle screw stabilization/fusion of adjacent vertebrae to stimulate bone regrowth over the screws to better camouflage the implants.

According to a preferred embodiment, the devices described herein are used to enable communication between two or more entities with at least one entity being a living organism. The other entities may be other living organisms of the same or a different species as the first living organism, or may be a machine including but not limited to a computer, a laptop, a cell phone, a personal digital assistant (PDA), a keyboard, a camera, a wheel chair, a bicycle, a car, etc. The communication can be one-way, two-way, or a multichannel exchange amongst several different entities (group conversation, or different entities all communicating with a centralized hub).

In this method of enabling communication between at least one living organism and at least one other entity a device comprising an effector and a sensor is implanted in the living organism. At least one additional component is implanted in the other entities to interact with this device. The sensor in the first entity (living organism) gathers data and generates a pulse that transmits the data to the other entities. The other entities receive the pulse through their components that read and translate it. In this manner the first entity (living organism) can relay information or "talk" to the other entities in open loop communication. In an alternative embodiment, the device in the first entity further comprises at least one feedback component and the communication is closed loop with the feedback component in the first entity verifying receipt of the pulse from the first entity by the second entity.

When receivers or transceivers are used to receive signals they may be used alone to receive signals directly or they may be used in conjunction with one or more intermediary devices that relay and/or process the signal prior to its reception. The intermediary device might amplify or reformat the signal and eliminate noise. In some embodiments, for some applications, the intermediary device could be something similar to a bluetooth earpiece, a cell phone, a wifi router, an air card, etc. Likewise, when effectors are used to induce an effect in an entity (machine or organism) they may induce the effect directly or through one or more intermediary devices that adjust or process the raw information and energy they provide.

The devices described herein are contemplated to be adaptable for use with state-of-the-art sixth sense and mind control devices. The minimally invasive implants of the present invention may be more convenient than headgear and may be used to read neural states and objectives to initiate actions in the outside world rather than relying on hand gestures from the living organism subject or patient. As used herein (before and after), the term "patient" refers to any object that subjects itself or is subjected to a treatment incorporating the present invention. A "patient" need not be an ill person or someone with physical, emotional, or psychological impairments or abnormalities. In fact, a "patient" need not be a human being or even a living organism. A "patient" may include completely healthy, happy, and successful organisms or objects that choose to subject themselves to treatment or are subjected to treatment with the present invention in order to further their abilities and become even more successful or to improve certain functions.

Examples of conditions the devices of the present invention can be used to treat include: psychological conditions generally, genetically or biologically based psychological conditions, depression, acute mania, bipolar disorders, hallucinations, obsessions, obsessive compulsive disorder, schizophrenia, catatonia, post-traumatic stress disorder, drug and alcohol addiction, Parkinson's disease, Alzheimer's disease, epilepsy, dystonia, tics, stuttering, tinnitus, spasticity, recovery of cognitive and motor function following stroke, pain syndromes, migraine, neuropathies, back pain, internal visceral diseases, urinary incontinence, etc.

Specific medical applications include using the cranial implants of the present invention as follows: (i) enabling a paralyzed man to send signals to operate a computer by "telepathically" moving a mouse, cursor, or typing on a keyboard, improving one's ability to work; and (ii) enabling a paralyzed man to send a signal causing a machine or computer to speak a phrase or message for them so that they can communicate their needs, desires, and thoughts to others and the world.

Specific entertainment and social applications include using the cranial implants of the present invention as follows: (i) a person has a Cranion™ implanted so that he can use it to control his iPhone or Wii game console without using his hands or in addition to hand controls; and (ii) a person has a Cranion™ implanted to communicate with one or more other persons, each with his own Cranion™ implanted to enable private "telepathic" conversations in a group of people including at a meeting, in church, in the courtroom, at a sporting event, and during a card game.

Implanted devices of the present invention (especially those in the brain) may be used to control a projector, a camera, a laser, a bar code reader, etc. worn on the body. Such sixth sense and mind control devices may find application for video games, electronic transfers of money, trading stocks, shopping, social and professional networking and storage of data about people, filming, photography, etc. The implants could be used to read expressive conditions (facial expressions, gestures) and emotional experiences (affective response) of the living organism in which they are implanted or of others with whom the patient comes in contact. The implants could then process and analyze this information to initiate cognitive actions in response thereto.

It is known that an electrical signal at the cortex of the brain looks random across the population for the same thought, even though it originates from the same region of the brain, due to a unique fold pattern of each person's brain similar to fingerprints. Headgear uses a mathematical algorithm to unlock the random signal to make it consistent across the population. Alternatively, the implants of the present invention might be used (i) to read the signal from a source in the brain beyond the cortex where it is uniform without the algorithm, (ii) apply the algorithm to data read at the cortex, or (iii) to provide an initial equilibration process that compensates for the differences in signals from one person to another.

According to still other embodiments, the Cranion™ has a longer electrode lead that passes through the skull at an angle and goes epidural to distant areas like a spinal cord stimulator sliding up the epidural space in the spine. This tip may then be steerable, for example, with a magnet.

Figure 7:
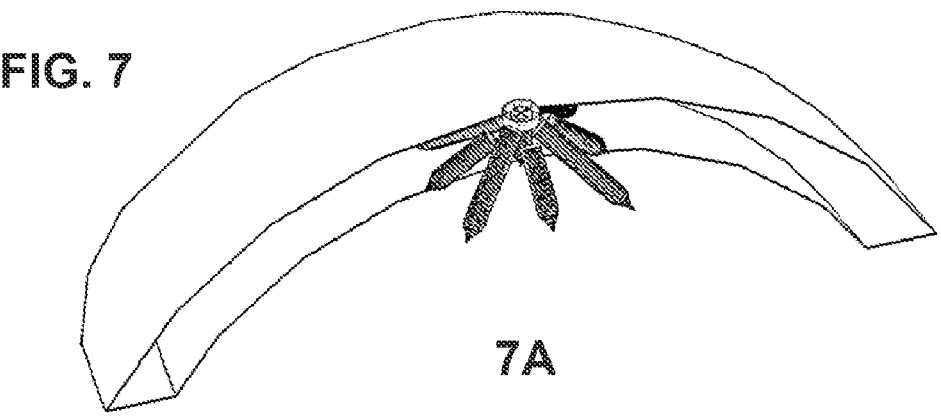
FIG. 7 illustrates a device comprised of nine different shafts placed through a single partial small burr-hole. The overall configuration is demonstrated in the cross section of the skull model with three different views in (A), (B), and (C). A top view (D) and bottom view (E) demonstrate the arrangement of the contacts that penetrate through the inner cortex to affect the brain. Four shorter shafts are configured in a "+" configuration while four longer shafts are inserted in an "X" pattern. A central shortest shaft is inserted last. This configuration results in a 3 by 3 matrix of components that can reach the cortex. This type of configuration is useful for epilepsy stimulation where the central electrode senses seizure activity at the seizure focus. This central electrode then activates its own stimulation electrode to abort the seizure. At the same time, the 8 surrounding ring of electrodes are activated as well. The activation of the ring of electrodes help to trap and cancel the spreading wave of seizure activity from the central epileptogenic focus. Such a configuration would generally necessitate a craniotomy; however this configuration is placed through a single partial burr hole.
Figure 7:
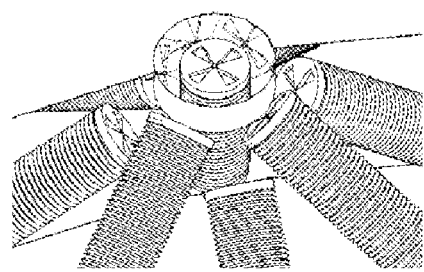
Figure 7:
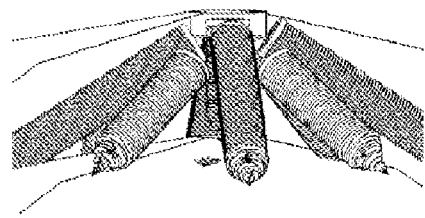
Figure 7:
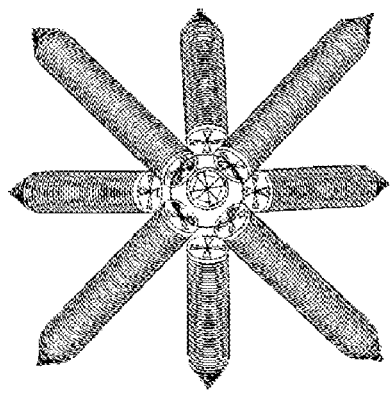
Figure 7:
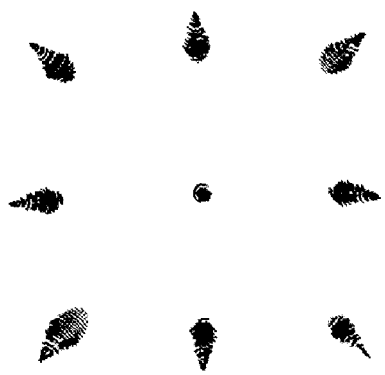
Figure 8:
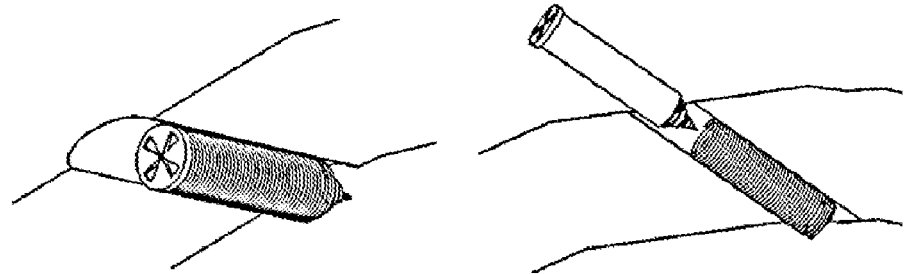
FIG. 8 illustrates a shaft inserted at an axial angle that serves as a conduit for a guidable and steerable epidural or subdural electrode array.
Figure 8:
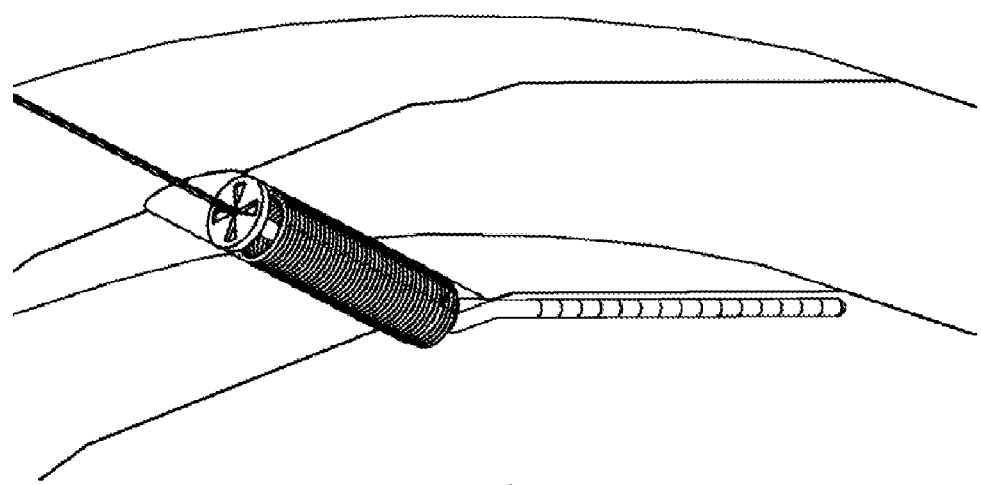
Figure 9:
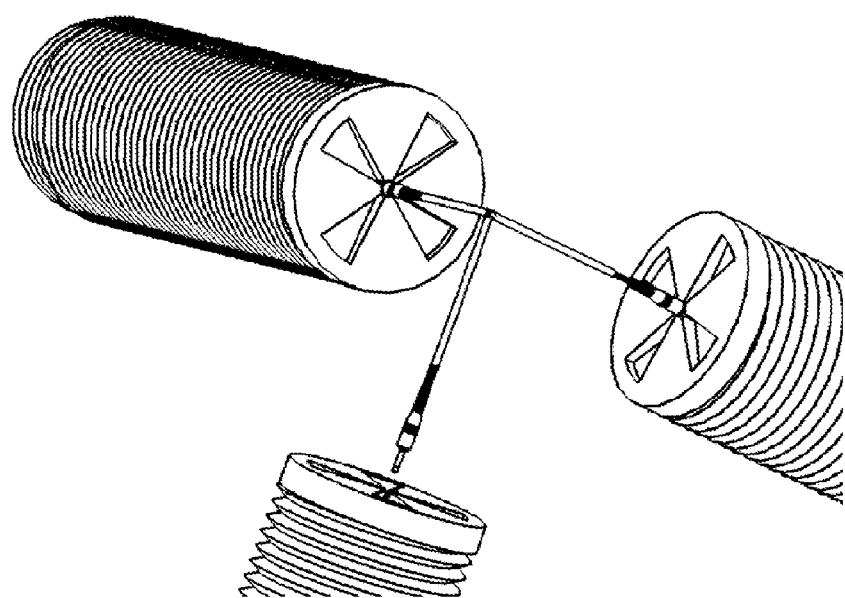
FIG. 9 demonstrates a simple connection system to physically link multiple shafts and components that are placed through a single or nearby entry sites. The connector shown is a multichannel connector, but any connector would suffice including USB or micro USB connectors. While the components can communicate wirelessly with each other with the appropriate components included within the shaft, some functions are more efficient through direct physical connections.
Figure 10:
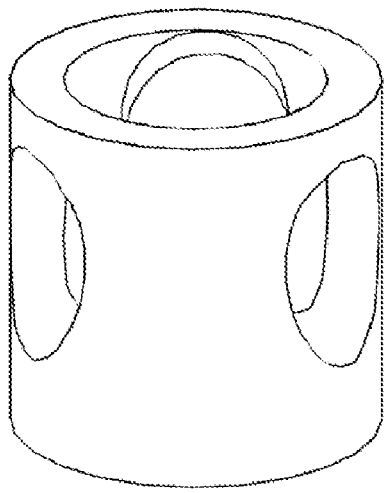
FIG. 10 demonstrates a preconfigured head unit used to facilitate the placement of multiple shafts and multi-component arrays.
Figure 10:
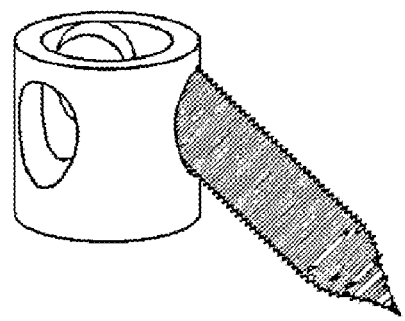
Figure 10:
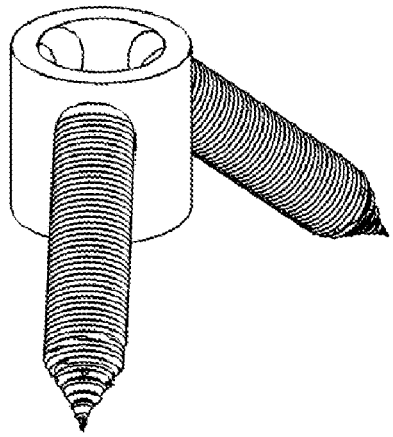
Figure 10:
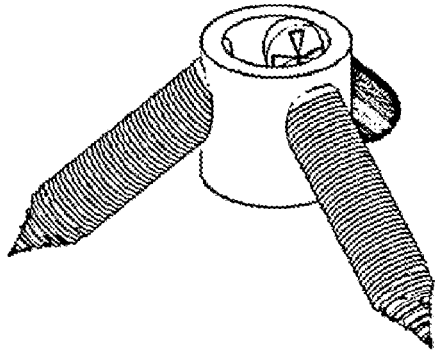
Figure 11:
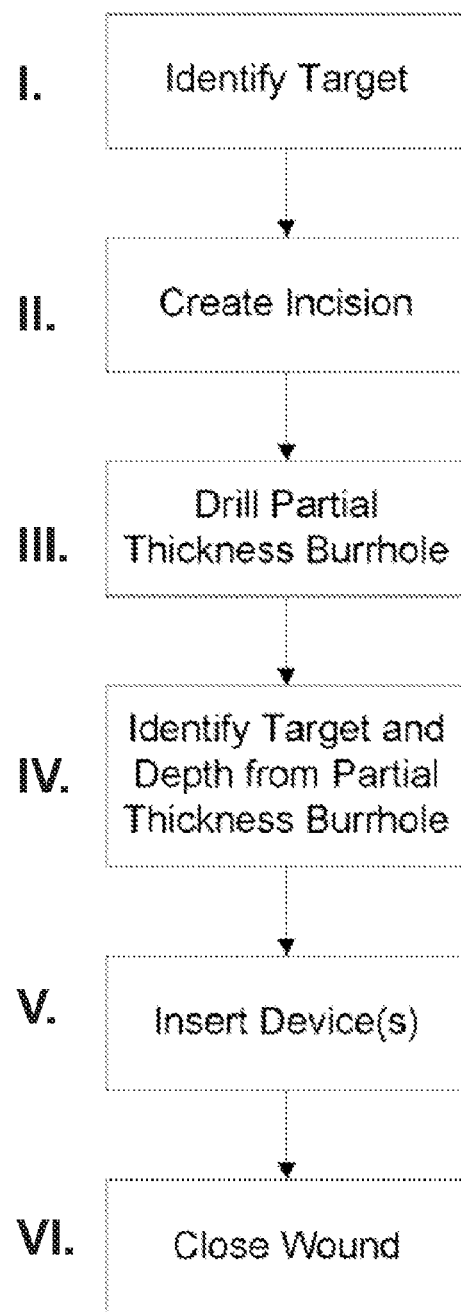
FIG. 11 shows a flow chart of a method of implanting the devices described herein: (I) identify the target, (II) create an incision, (III) drill a partial thickness burrhole, (IV) identify target and depth from partial thickness burrhole, (V) insert device(s), and (VI) close wound.

The general method, as summarily illustrated in the flow chart of FIG. 12, in greater detail may encompass the following sequence:

1.) Use stereotactic localization, either with a frame or frameless stereotactic localization to identify a target(s);

2.) Decide on a configuration. For example, either single electrode, multiple around the single target, single line (see FIGS. 7 and 8);

3.) Single stab incision 5-10 mm;

4.) Drill 2-4 mm partial thickness burrhole (this allows an "edge" so that drills can be angled into the corner and an off angle trajectory can be accomplished;

5.) Use stereotactic localization to identify target and depth away from the central partial burrhole;

6.) Plan trajectory based on the target and either drill a pilot hole or use a self drilling, self tapping Cranion™ to insert the Cranion™ device;

6a.) Drilling a pilot hole allows exact knowledge of the depth of the hole however a cannulated Cranion™ in which the sharp tip can be removed (see FIG. 9) also allows a portal to determine whether the epidural space has been entered 7.) Place other Cranions™ and connect them with wires (see FIG. 9) or have them connect wirelessly. Or, use the head device.

8.) Add other components such as extra batteries that don't need to go all the way out of the skull.

9.) Close the wound

The present invention is not limited to the embodiments described above. Various changes and modifications can, of course, be made, without departing from the scope and spirit of the present invention. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents. As used in the claims the conjunction "or" means the inclusive or (and/or, either element independently or any combination of the elements together).

What is claimed is:

1. A method of gathering data about or providing electrical stimulation therapy to a patient's brain, the method comprising:
   creating an incision at an entry site in the patient's scalp;
   drilling a partial burrhole in the patient's skull through the incision at the entry site;
   implanting a first shaft comprising a first sensor or effector in the patient's skull by passing the first shaft through the incision and partial burrhole and into the skull, wherein when the first shaft is fully inserted along a first trajectory, a proximal end of the shaft passes through the incision and burrhole, thereby allowing for another shaft to be inserted at a different trajectory; and implanting a second shaft comprising a second sensor or effector in, the patient's skull by passing the second shaft through the incision and partial burrhole and into the skull, wherein the second shaft is implanted along a second trajectory that is different than the first trajectory, and wherein when the second shaft is fully inserted along the second trajectory, a proximal end of the shaft passes through the incision and burrhole, thereby allowing for another shaft to be inserted at a different trajectory;

wherein each of the first and second shafts is configured to be inserted at an angle between and inclusive of parallel to a tangent of a surface at the incision and perpendicular to a tangent of a surface at the incision; and wherein a length of the second shaft is independent of the first shaft and the lengths of the first and second shafts are not limited to the thickness of the skin, muscle, tissue, bone, or skull at the entry site.

2. The method of claim 1, wherein the lengths of the first and second shafts are selected such that the first and second shafts do not pass into the patient's brain.

3. The method of claim 1, further comprising identifying at least first and second targets in the patient's brain.

4. The method of claim 1, wherein the incision has a length of about 5-10 mm.

5. The method of claim 1, wherein the burrhole has a depth of about 2-4 mm.

\* \* \* \* \*